(12) United States Patent
Taylor et al.

(10) Patent No.: US 6,546,818 B2
(45) Date of Patent: Apr. 15, 2003

(54) COMBUSTIBLE GAS MEASUREMENT APPARATUS AND METHOD

(75) Inventors: Brian Taylor, Calgary (CA); Wiktor Skupinski, Calgary (CA)

(73) Assignee: Pason Systems Corp., Calgary (CA)

( * ) Notice: Subject to any disclaimer, the term of this patent is extended or adjusted under 35 U.S.C. 154(b) by 0 days.

(21) Appl. No.: 10/186,385

(22) Filed: Jul. 1, 2002

(65) Prior Publication Data
US 2003/0019304 A1 Jan. 30, 2003

Related U.S. Application Data

(62) Division of application No. 09/849,281, filed on May 7, 2001.

(30) Foreign Application Priority Data

Apr. 23, 2001 (CA) .............................................. 2344842

(51) Int. Cl.[7] .............................................. G01N 1/00
(52) U.S. Cl. .................................................. 73/863.03
(58) Field of Search ......................... 73/863.01, 863.02, 73/863.03, 25.03, 23.31

(56) References Cited

U.S. PATENT DOCUMENTS

| | | | | |
|---|---|---|---|---|
| 4,555,931 A | * | 12/1985 | Amimoto et al. | 73/23.2 |
| 5,110,747 A | * | 5/1992 | Pataschnick et al. | 436/133 |
| 6,062,092 A | * | 5/2000 | Weaver | 73/863.03 |

* cited by examiner

*Primary Examiner*—Robert Raevis
(74) *Attorney, Agent, or Firm*—Terry L. Leier; Blake, Cassels & Graydon LLP

(57) ABSTRACT

Discloses a system for the analysis and measurement of selected gases such as combustible gases contained in a gaseous sample to be analyzed including a mixing manifold arrangement to mix the sample gas with a diluting gas to provide a constant gas output flow rate to a detector system. The mixing manifold arrangement automatically reconfigures itself to provide an optimal concentration ratio of sample and diluting mixed gas to the detector system. A constant sample gas input rate is preferred. Excess sample gas not required to maintain a constant mixed sample output rate is discharged.

9 Claims, 4 Drawing Sheets

COMBUSTIBLE GAS MEASUREMENT APPARATUS AND METHOD

This is a divisional of co-pending application Ser. No. 09/849,281 filed May 7, 2001.

FIELD OF THE INVENTION

This invention relates to a system for the analysis and measurement of selected gases and, more particularly, for measurement of combustible gases such as hydrocarbon gases contained in a gaseous sample to be analysed.

BACKGROUND OF THE INVENTION

There is a demand for information indicating the hydrocarbon content of gaseous mixtures. For example, the return flow drilling mud material discharged from an oil or gas exploration well can contain entrained hydrocarbon gases. Detection and measurement of the hydrocarbon gas content of the well return material can be used to give an indication of when a certain zone is being penetrated in the well drilling process. Such data can provide information to the geology personnel on the drilling project to enable them to form an assessment or provide an indication as to whether the well drilling has hit a producing zone. In oil and gas exploration, the primary hydrocarbon gas of interest is generally methane, although, under certain drilling conditions, there is also interest in information relating to some of the other hydrocarbon gases that may be present.

The current state of the art uses a variety of apparatus and methods to quantify and qualify the hydrocarbon content of a gas sample, that is, to perform analysis of the sample. The simplest types of apparatus to perform analysis of a gas sample, are systems that use a "thermal conductivity detector" (TCD). Thermal conductivity detectors are suitable when the gas to be analyzed by the detector contains a known gas in a known carrier gas. This is often referred to as binary analysis of gas. Every gas has a unique thermal conductivity as one of its properties. Thermal conductivity detection works best when the carrier gas and the sample gas have very different thermal conductivities. Typically, the TCD detector has a Wheatstone bridge arrangement where the detector element manifests a decrease in resistance with increasing thermal conductivity of the sample gas. By way of example, U.S. Pat. No. 3,683,671 to Van Swcray entitled Measuring System Including Thermal Conductivity Detector Means provides an electrical circuit bridge excited at one power node, by a clamped square wave arm at another power node by a feedback circuit. The output of the circuit bridge is fed to a demodulator to generate an output signal representative of the sample being sensed.

A Wheatstone bridge and visual indicator in the form of light emitting diodes in a gas analyser arrangement is disclosed in U.S. Pat. No. 4,028,057 to Nelson. These detectors are used in gas chromatography where a carrier gas that has a very high thermal conductivity, such as helium, is used. When a sample that has a much lower thermal conductivity than helium is introduced into the carrier gas the output of the detector will show a change relative to the amount of sample contained within the carrier. A thermal conductivity detector can be confused, that is produce erroneous output, if more than one type of sample gas is introduced into the carrier gas. That is if the thermal conductivity detector is used to analyse a gas mixture of multiple sample gases. For example, if one of the sample gases has a higher thermal conductivity than the carrier gas and the second sample gas has a lower thermal conductivity than the carrier gas, then the detector output may not even change for varying constituent gas compositions or mixtures.

Thus, a thermal conductivity detector is not well suited to analysis of hydrocarbon gases entrained in well returns for a number of reasons. First, it is not feasible to transport large tanks full of helium to the well site. Consequently, the carrier gas that is generally used is air. Air has a thermal conductivity of 1.00 and methane a thermal conductivity of 1.3. This means there is not a very good signal to noise ratio between the air carrier and the gas of interest, which makes a thermal conductivity detector based instrument prone to drifting. Notwithstanding their drawbacks, such thermal conductivity detectors are in use in analyzers used in the oil well drilling industry. However, because of the inherent limitations of using TCD detectors in these environments, it is not uncommon to need to zero the baseline of a TCD based system on an hourly basis. Automated baseline adjustment apparatus have been proposed to compensate for temperature changes in such systems. For example, the arrangement proposed by Hagen in U.S. Pat. No. 4,817,414.

Also, thermal conductivity detectors are, by their nature, sensitive to ambient temperature. Even a 1 degree shift in ambient temperature will cause a noticeable shift in the baseline of a thermal conductivity detector operating in this low signal to noise ratio configuration.

Another, somewhat more sophisticated detection apparatus employs a catalytic combustion detector (CCD) to detect the presence of hydrocarbons. For example, U.S. Pat. No. 3,607,084 to Mackey for Combustible Gas Measurement describes passing a stream of gas containing the combustible gas analytes over a conductive metal wire coated with a think catalytic coating which is at a temperature at which oxidation of the gases is initiated. Numerous other arrangements of CCD apparatus are known for example, U.S. Pat. No. 4,045,177 to McNally, U.S. Pat. No. 4,072,467 to Jones, U.S. Pat. No. 4,111,658 to Firth et al, U.S. Pat. No. 4,123,225 to Jones et al, and U.S. Pat. No. 4,313,907 to McNally are examples of such CCD detectors. CCD's are sensitive to anything that is combustible and in an oil and gas well drilling environment, hydrocarbon gases are the combustible gases that would be encountered. This means a CCD can be used as to provide a measurement of the total hydrocarbon content of a gas without regard to the particular type of hydrocarbon gas. While a CCD will respond to combustible compounds other than hydrocarbons, it is the gaseous hydrocarbon compounds that will be of interest in the sample gases recovered from the drilling mud in a well drilling environment. A major problem with CCD's is their limited range. If a CCD is subjected to explosive combustible gas concentrations, that is concentrations between the upper and lower explosive limits of that compound, they are destroyed as the gas actually combusts and coats the detector surface with carbon, rendering it ineffective after that point. For methane the lower explosive limit is 5% in air. An air mixture containing methane gas concentrations greater than the 5% lower explosive limit will result in a mixture that becomes explosive.

To obtain the benefit of a stable baseline and wider range of methane concentrations in a sample, two detector systems have been produced. Current state of the art two-detector apparatus uses a CCD sensor to around 4% concentration in the mixture. Above that point, the sensor apparatus control turns off the CCD sensor and passes the sensing over to a thermal conductivity sensor. A thermal conductivity sensor, of course, has all of the problems as described above. However, a major advantage of a two-detector analyser is a more stable baseline.

A combined CCD and thermal conductivity analyzer has some major drawbacks if a gas other than methane is present in the sample to be analyzed. For instance, if C2 is the gas being presented to the CCD, the CCD will detect its presence very nicely. However, when the analyzer switches over to the thermal conductivity detector, the C2 gas may not be detected at all. The system will respond by switching back to the CCD which ultimately causes the system to keep switching back and forth between the two sensors and can result in the destruction of the CCD due to exposure to explosive levels of C2 gas in the sample. An example of a two-detector system is shown, for example, in U.S. Pat. No. 4,804,632 to Schuck et al which switches from one sensor to another based on set sample temperatures and holding the sensing devices to a preset temperature.

Another gas detection system using a CCD detector, operates by diluting the sample with air when it exceeds 4% as shown, for example, in U.S. Pat. No. 3,771,960 to Kim et al. Adding diluting air to the sample allows such a gas detection system to use a CCD sensor throughout the entire range. Generally, such gas detection system apparatus provides preset ranges, for example 0% to 3% which is the undiluted range and a second dilution range, for example 0% to 100%. In one prior art arrangement, the dilution is accomplished by using a manifold with orifices drilled into it that give approximate volumes of gas for the dilution blending. An on/off valve is used to control the diluting of the sample with air. This system requires precise adjustment of needle valves in the factory before being shipped. A problem with this dilution approach is that gas concentrations vary considerably with pressure and temperature and thus are very hard to control precisely enough to give an accurate reading when there is a switch over from one range to the other. In addition to the pressure temperature aspects of the dilution blending problem, a further problem inherent in this method is that the dilution is very hard to effect without either reducing the sample drawn from the extraction device or increasing the amount of sample passed through the detector.

In conventional combustible gas analysers, a constant flow rate through the detector is maintained by reducing the amount of sample drawn from the sample source or extractor. On the other hand, where a constant flow rate from the sample source or extractor is maintained, an increase in the flow rate through the detector is caused by the air added to or blended with the sample to produce the diluted mixture flowing through the detector. Neither of these situations is optimal. Drawing less sample gas from the gas trap or sample extractor can cause the concentrations to rise as the gas trap is extracting gas from the drilling mud at a certain rate. If the rate of sample extraction is suddenly reduced, then there will be a build up of sample gas inside the extractor. On the other hand, if the extraction rate is kept constant, the addition of diluting gas will cause the volume of the diluted sample gas mixture produced to increase with a corresponding increase in the sample flow rate through the detector. Changes in sample flow rates through a CCD detector will consequently change the response of the detector, as the detector response is dependent on sample flow rates to the detector. To give accurate results, CCD detectors require a precise flow rate. In operation, a CCD detector actually destroys sample that it comes in contact with, so, at low flow rates, the readings will drop off as there is more and more dead sample in contact with the detector.

SUMMARY OF THE INVENTION

To overcome these shortcomings, in one of its aspects, the invention provides a sample gas dilution system to control the supply of a sample gas to a detector supply port for supply to a sample detector system. The gas sample dilution system is arranged with three gas flow controls. A sample gas flow control is provided to control input sample gas flow to a detector supply port. A diluting gas flow control is provided to control supply of a diluting gas to the detector supply port and therefore control blending of the sample gas with the diluting gas. An exhaust flow control is provided to control an exhaust flow of excess sample gas not required by a sample detector system coupled to the detector supply port. A controller, such as a computer, provides the settings of the flow controls. In the preferred manner of operation, the controller operates the flow controls to keep the input sample gas flow rate into the sample dilution system constant and the gas flow to the detector supply port constant. That is, the controller operates the sample gas flow control, the diluting gas flow control, which controls blending of the sample gas with a diluting gas supply, and the exhaust flow control which controls an exhaust flow of the sample gas to maintain a constant input sample gas flow rate from the gas sample source and a constant output flow rate to the detector system. Excess sample gas not required for supply to the sensor block of the sample detector system is exhausted from the apparatus.

In the preferred embodiment, each gas flow control has a proportional control valve responsive to a control signal to control the flow of gas therethrough. Preferably closed-loop controlled mass flow controls are utilized to facilitate precise control of gas quantities and flow rates. In a closed-loop controlled gas flow control, the gas flow control includes a flow sensor to produce signalling representative of the gas flow rates therethrough. The flow sensor provides a feedback signal that is used in the control of the proportional control valve to facilitate closed-loop control of the proportional control valve based on feedback from the flow sensor.

In another aspect of a preferred embodiment of the invention, the sensor block or detector system operates in conjunction with the sample dilution system to allow for several ranges to be implemented yet keep the signal to noise ratio from the detector devices at optimum levels. One preferred embodiment discloses ranges of 0% to 4%, 0% to 8%, 0% to 16%, 0% to 32%, 0% to 64% and 0% to 100%. An algorithm for automatic range selection permits optimal sensor block utilisation with minimal user intervention while providing an output representative of combustible gas concentrations in the sample gas without the need to configure or reconfigure the instrument manually.

In one of its aspects, the invention provides an apparatus for mixing gases comprising a manifold forming a diluting gas port, a sample inlet port and a detector supply port all in common communication with each other. A diluting gas flow control means is provided which is operable to control a flow of diluting gas through the diluting gas port in response to a first control signal. A sample gas flow control means is operable to control a flow of sample gas to the detector supply port in response to a second control signal. A detector means in communication with the detector supply port is operable to produce output signalling representative of the content of a selected gas of a gas mixture passing therethrough. A control means is provided to produce the first and second control signals for respective diluting gas and sample gas flow control means whereby any gases supplied to the manifold are mixed therein and expelled through the detector supply port in proportions set by the control means.

In another of its aspects, the invention provides an apparatus for mixing gases comprising a manifold forming a sample gas inlet port, an exhaust port, a diluting gas inlet port and a detector supply port all in common communication with each other. A diluting gas flow control means is operable to control a flow of gas through the diluting gas inlet port in response to a control signal. A sample gas flow control means is provided to control a flow of sample gas to said detector supply port in response to a control signal. An exhaust gas flow control means is provided to control a flow of gas through the exhaust port in response to a control signal. A control means includes means to receive a detector signal output, the control means produces a respective control signal for the diluting gas flow control, sample gas flow control and exhaust gas flow control means is included whereby a constant rate of gas flow through said detector supply port is obtained. The sample gas supplied to the sample gas inlet port and the diluting gas supplied to the diluting gas inlet port are mixed and expelled through the detector supply port in proportions set by the control means responsive to a received detector signal output.

And in yet another of its aspects, the invention provides a method of measuring a gas mixture comprising: receiving a sample gas from a source at a predetermined sample gas flow rate, supplying a gas mixture to a detector at a predetermined detector supply gas flow rate and receiving a detector signalling produced by a detector monitoring the supplied gas mixture. Periodically the received detector signalling is compared to a predetermined range. A supply of diluting gas is mixed with a selected portion of the sample gas flow to supply the gas mixture at the predetermined detector supply gas flow rate and yet maintain the received detector signalling within the predetermined range.

Preferred embodiments of the invention will now be described with reference to the attached drawings. For convenience, like reference numerals have been used to depict like elements of the invention throughout the various drawings.

DETAILED DESCRIPTION OF THE PREFERRED EMBODIMENTS

For the discussions contained herein, "flow controller" and "flow control" will refer to any actuator used to regulate the flow by volume or mass of a selected gas to a predetermined set point. Preferably, the flow control or flow controller has a sensor, that is, either a flow sensor or a mass flow sensor paired with the actuator valve arranged and used in a closed-loop fashion. In the arrangement of the measurement apparatus and method of operation of it, the concepts of mass flow and volume flow presented herein are used interchangeably. Gases supplied at a constant pressure can provide a constant mass flow. At a constant temperature and pressure the mass of a gas will be linearly proportional to its volume, so using mass sensors or flow sensors accomplishes the same thing. A sensor and actuator valve in a paired arrangement and used in a closed-loop fashion can be used to regulate the flow of a gas by volume or by mass. Thus it will be understood that mere rearrangement of the relative positions of an actuator valve and flow sensor in a gas path, or choosing a different control algorithm does not depart from the spirit or scope of the invention as defined in the claims appended hereto. Thus, in the discussion that follows, "flow" will refer to any quantity of a selected gas, measured by volume or mass.

Figure 1:
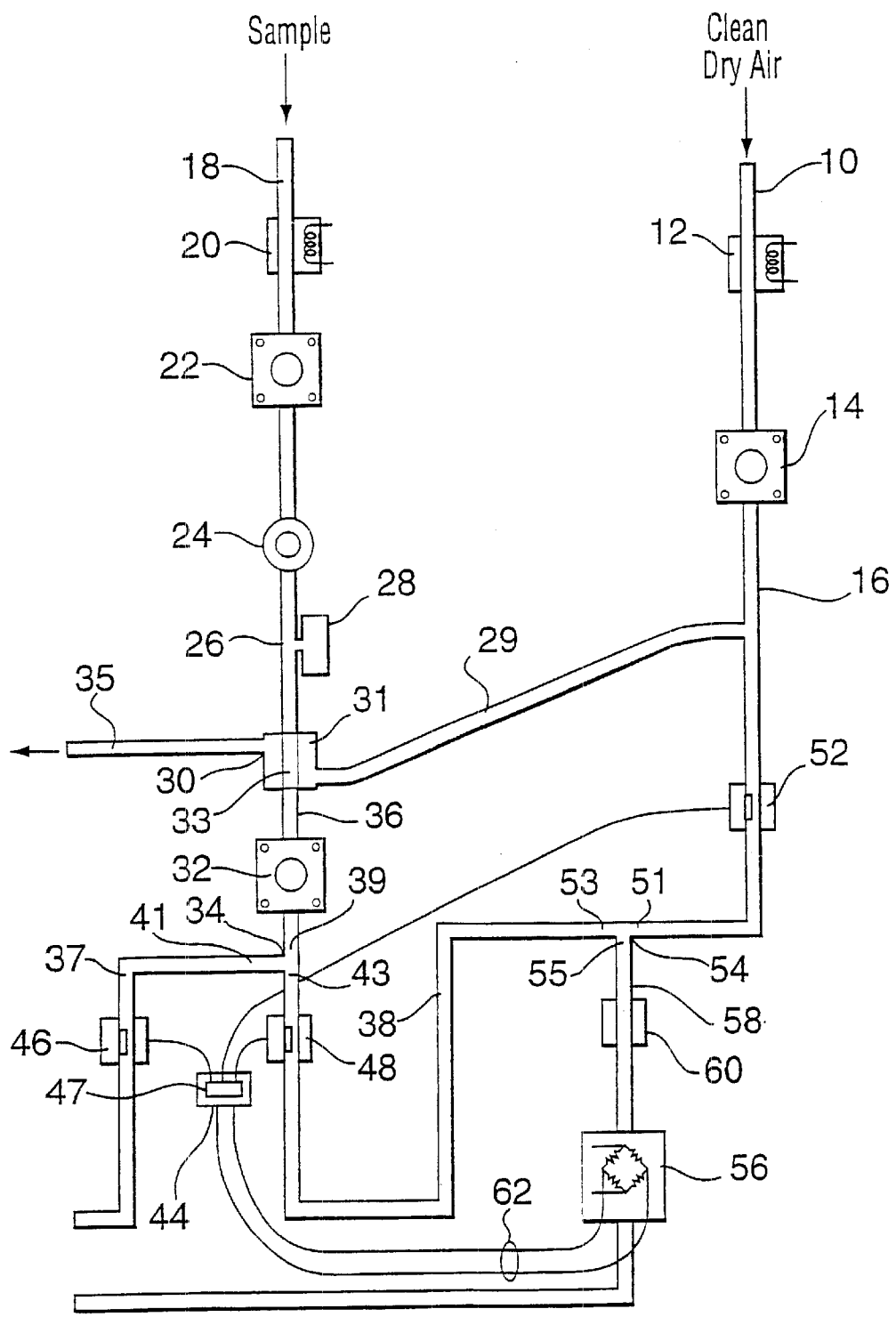
FIG. 1 is a schematic representation of an embodiment of a sample dilution system control in accordance with the invention.

FIG. 1 shows, in a schematic diagram form, an embodiment of a sample dilution system of a gas analyzer in accordance with the invention. The sample dilution system is provided with a source of pressurized clean dry diluting gas, preferably air, for supply to conduit 10. This air passes through a heater 12 to heat the air to a predetermined uniform temperature as required, for example, 40° C. The heated air is then passed to a regulator 14 to obtain a predetermined uniform air pressure. The temperature and pressure conditioned air is supplied to conduit 16. The gas sample to be measured is supplied to sample tube 18 where it is delivered to systems to condition the sample to obtain predetermined or pre-set uniform properties. A heater 20 heats the sample to a predetermined temperature, for example, 40° C. A first filter assembly 22 removes any particulate matter and airborne liquid or condensed humidity from the sample. A suitable filter for this purpose is a coalescing filter capable of removing 99.9% of any oil or water droplets and particulate contamination, preferably to the 0.01 micron level. A pump 24 is used to draw air from the sample source into sample tube 18.

The sample discharged from pump 24 is supplied to conduit 26 and perturbations in pressure caused by operation of pump 24 are absorbed by ripple chamber 28. The sample is then fed through a dehumidifier 30 to dry the sample to a dew point approaching −40° C. A suitable dehumidifier is a counterflow exchange membrane dryer fabricated from perfluorinated tetraflouroethylene copolymer membranes, for example, Nafion (trademark) membrane tube counter flow dryers available from Perma Pure Inc in the MD series gas dryers can be used to dry the sample air. To operate the dehumidifier 30, a source of dry conditioned air is provided by air supply conduit 29 that interconnects the dry conditioned air contained in supply line 16 to the dehumidifier 30. The dry air supplied to dehumidifier 30 passes through an inner chamber or annulus 31 of dehumidifier 30 in contact with the exterior surface of the Nafion (trademark) membrane tube 33. The dry air picks up moisture from the sample gas passing though the lumen of membrane 33. The moisture extracted from the gas sample by dehumidifier 30 into the counter flowing dry air flowing in annulus 31 is expelled to the atmosphere by discharge line 35. The dried sample gas is output from dehumidifier 30 into conduit 36.

A liquid filter 32, for example, a micro porous membrane filter constructed from expanded polytetrafluoroethylene (for example, Teflon*trade mark) is provided as a failsafe to remove any particulate matter that may still be present in the sample stream. A manifold 34, for example a T-junction, forms a sample port 39 to receive the gas sample. Manifold 34 communicates the gas received in sample port 39 to two ports each providing a path for the filtered, dehumidified sample gas to flow along. A first port, namely, a sample exhaust or discharge port 41, is coupled to a surplus sample discharge line 37 and the other port, common port 43, is in communication with sample feed or detector supply line 38 to deliver the sample gas toward the detector system. Sample gas flows through lines 37 and 38 are controlled by gas flow control means 46 and 48 respectively.

Control of the flow sample gas through discharge line 37 and sample feed line 38 is controlled by gas flow control means, comprising a sample exhaust or discharge valve 46 and sample valve 48 respectively. These flow control means are each responsive to signalling received from controller 44. In this manner, the sample gas passing through sample feed line 38 is under complete control of controller 44. To provide for more accurate and precise operation and control of the gas flow control valves, a closed loop feedback is preferably implemented as will be explained with reference to FIG. 2. Controller 44 controls the flow of the gas sample exiting from manifold 34 through lines 37 and 38 respectively. The sample flow rates through lines 37 and 38 are set to provide for a uniform flow rate of the sample into manifold 34 through sample port 39 so as to provide a constant sample draw rate from the sample gas source, for example, 500 ml/minute.

The rate of flow of the diluting air, that is the clean dry air, in conduit 16 is controlled by a gas flow control means 52. A gas flow control means 52 is operated in response to signalling from controller 44 to control the rate of flow of the clean dry diluting air through conduit 16. Manifold 54 forms an inlet port 51 coupled to conduit 16 carrying the diluting air. Inlet port 51 is in communication with sample supply port 53 and detector supply port 55, formed by manifold 54. The supply of diluting air in conduit 16 and sample gas in conduit 38 are combined in manifold 54 and then supplied to the sensor block detector means 56 via detector supply port 55.

It is preferable that the gas flow into detector sample supply line 58 is constant to maintain a constant rate of gas flow into the sensor block detector means 56. A constant rate of gas flow results in a more reliable and repeatable reading from the sensor apparatus. Controller 44 adjusts the mass flow rate, of the diluting air by controlling the dry air gas flow control means valve 52 and of the sample gas by controlling the sample valve gas flow control means 48, to obtain a uniform mass flow rate of the gas mixture into detector sample supply line 58. For example, flow control means valves 48, 52 can be controlled to ensure that a constant flow of gas at the rate of 500 millilitres per minute of gas is presented to detector sample supply line 58. The gas present in detector sample supply line 58 is heated to a uniform temperature by heater 60, for example, to a temperature of 55° C. The heated sample is then presented to sensor block detector means 56, which produces an output representative of the hydrocarbon gases detected in the sample. The sensor block output is supplied to controller 44 on signal line 62 for processing in controller 44. On processing, the controller 44 may output the reading to display 47 for example, or, by supplying the reading in data form on a communications link to a central or a remote computer (not shown) for logging and display.

In the preferred embodiment, controller 44 operates to control the sample valve 48 and air valve 52 such that the ratio of sample gas to diluting is mixed at predetermined amounts. For example, a first ratio when the sample gas is known to be less than 4% can be used for calibration. For calibration, a known gas supply, for example 2.5%, is used and fed directly into the gas sample tube 18. In this calibration configuration, controller 44 adjusts the valves of the sample dilution apparatus to provide 100% of the sample volume and 0% of the diluting air volume to the sensor block detector means 56. In this calibration configuration, air supply valve 52 and discharge valve 46 are completely closed and sample valve 48 is controlled to allow a fixed flow, for example 500 ml/min. In this configuration of the dilution apparatus, none of the sample gas is exhausted and no diluting air is mixed with the sample gas before it enters the sensor block detector means 56.

Figure 2:
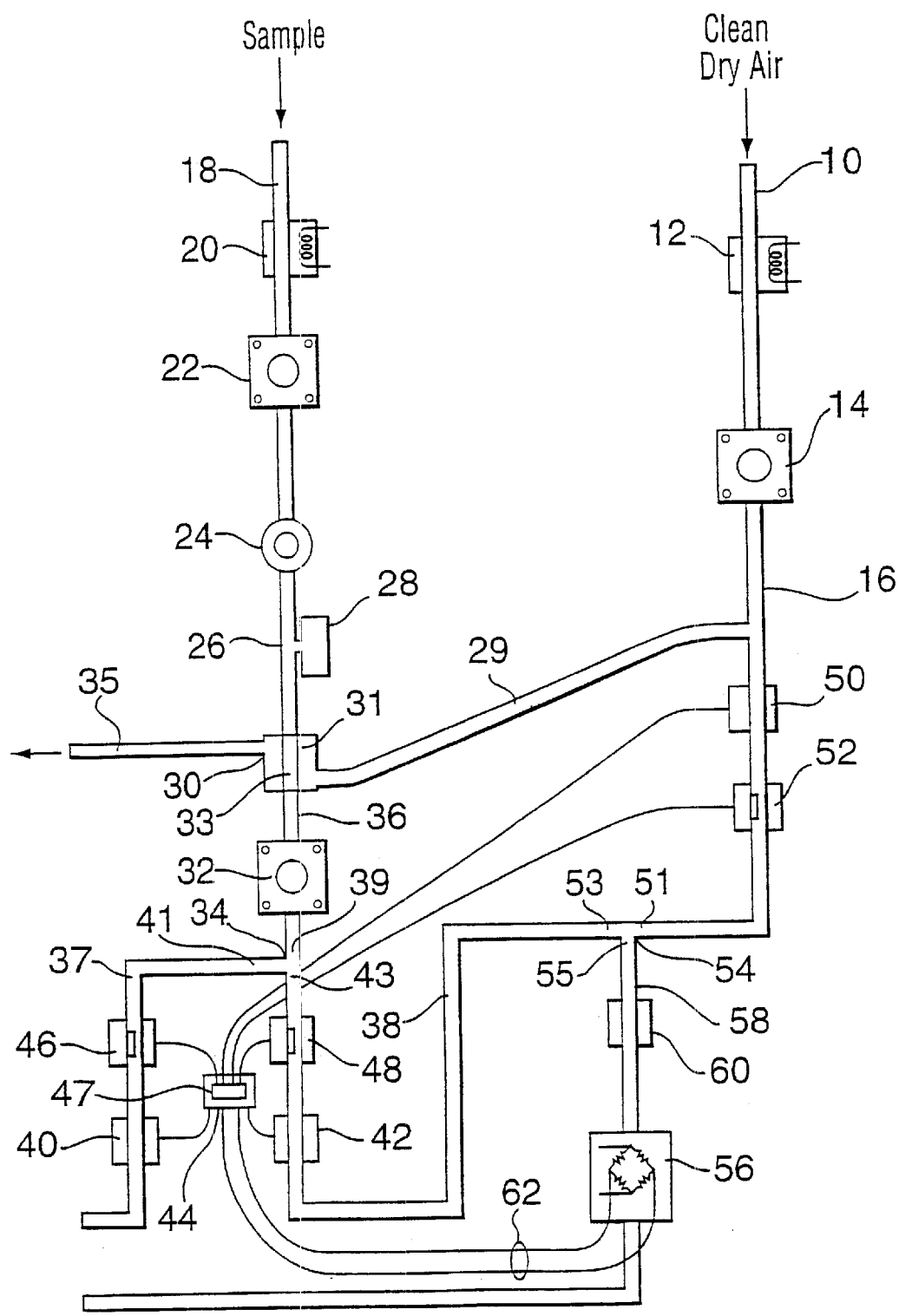
FIG. 2 is a schematic representation of an embodiment of a sample dilution system control of FIG. 1 including mass flow sensors.

FIG. 2 shows, in a schematic diagram form, a preferred embodiment of the sample dilution system of FIG. 1 that further includes gas flow sensors.

Control of the flow sample gas through discharge line 37 and sample feed line 38 is controlled by gas flow control means, comprising exhaust discharge valve 46 and sample supply valve 48 respectively. These flow control means are each responsive to signalling received from controller 44. In this manner, the sample gas passing through sample feed line 38 is under complete control of controller 44. To provide for more accurate and precise operation and control of the gas flow control valves, a closed loop feedback is preferably implemented. In this regard, a discharge mass flow sensor 40 and a sample mass flow sensor 42, for example, AWM Series Microbridge Mass Airflow sensors produced by Honeywell, provide an output proportional to the gas mass flow through each respective mass flow sensor. The outputs of mass flow sensors 40 and 42 are used to effect closed-loop control in a control loop. If desired, closed loop control can also be implemented with suitable processing in controller 44. Controller 44 sets the mass flow of the gas sample exiting from manifold 34 through lines 37 and 38 respectively. The mass flow rates through mass flow sensors 40 and 42 are preferably selected to provide for a uniform mass flow rate of the sample into manifold 34 to provide a constant sample draw rate from the sample gas source, for example, 500 ml/minute.

The rate of flow of the diluting air, that is the clean dry air, in conduit 16 is controlled by a gas flow control means 52. Preferably, the flow of air through the actuator valve of gas flow control means 52 is measured by a mass flow sensor 50 to obtain the benefit of closed loop control. In one embodiment, controller 44 effects closed loop control, or, in another embodiment, a local feedback loop controller can be used for closed loop control. A gas flow control means 52 is operated in response to signalling from controller 44 to control the rate of flow of the clean dry diluting air through conduit 16. Manifold 54 forms an inlet port 51 coupled to conduit 16 carrying the diluting air. Inlet port 51 is in communication with common port 53 and detector supply port 55, formed by manifold 54. The supply of diluting air in conduit 16 and sample gas in conduit 38 are combined in manifold 54 and then supplied to the sensor block detector means 56 via detector supply line 58.

In the preferred manner of operation of the embodiments of the invention depicted in FIGS. 1 or 2, controller 44 operates to control the sample valve 48 and air valve 52 such that the sample air ratio is mixed at predetermined amounts. For example, a fixed ratio can be configured and used for calibration when the sample gas is known to be less than 4%. For calibration, a known concentration gas supply is used, for example 2.5%, and fed directly into the gas sample tube 18. In this calibration configuration, controller 44 adjusts the valves of the sample dilution apparatus to provide 100% of the sample volume and 0% of the diluting air volume to the sensor block detector means 56. In this calibration configuration, air supply valve 52 and discharge valve 46 are completely closed and sample valve 48 is controlled to maintain a fixed flow, for example 500 ml/min. In this configuration of the dilution apparatus, none of the sample is exhausted and no diluting air is mixed with the sample before it enters the sensor block detector means 56.

Following is a Dilution Table, which sets out valve configurations that are set in a preferred method of operating the sample dilution apparatus. The sample dilution apparatus valve configuration settings provide an optimal operating range for supply of sample gas to the sensor block detector means 56. The optimal operating range has an upper threshold or limit to ensure that the maximum hydrocarbon gas concentration supplied to the sensor block detector means 56 does not exceed a maximum threshold concentration, for example, a 4% concentration. Also the valve configuration settings of the optimal operating range provide a lower threshold or limit which increases the mixing ratio of sample gas to diluting gas when the predetermined minimum concentration of sample gas supplied to the sensor block detector means 56 falls below the lower threshold. Reducing dilution of the sample gas when the detector sensor output falls below a predetermined threshold facilitates obtaining accurate readings from the sensors.

M—is the mixing ratio configured, and

S—is the gas concentration provided to the sensor block

Figure 3:
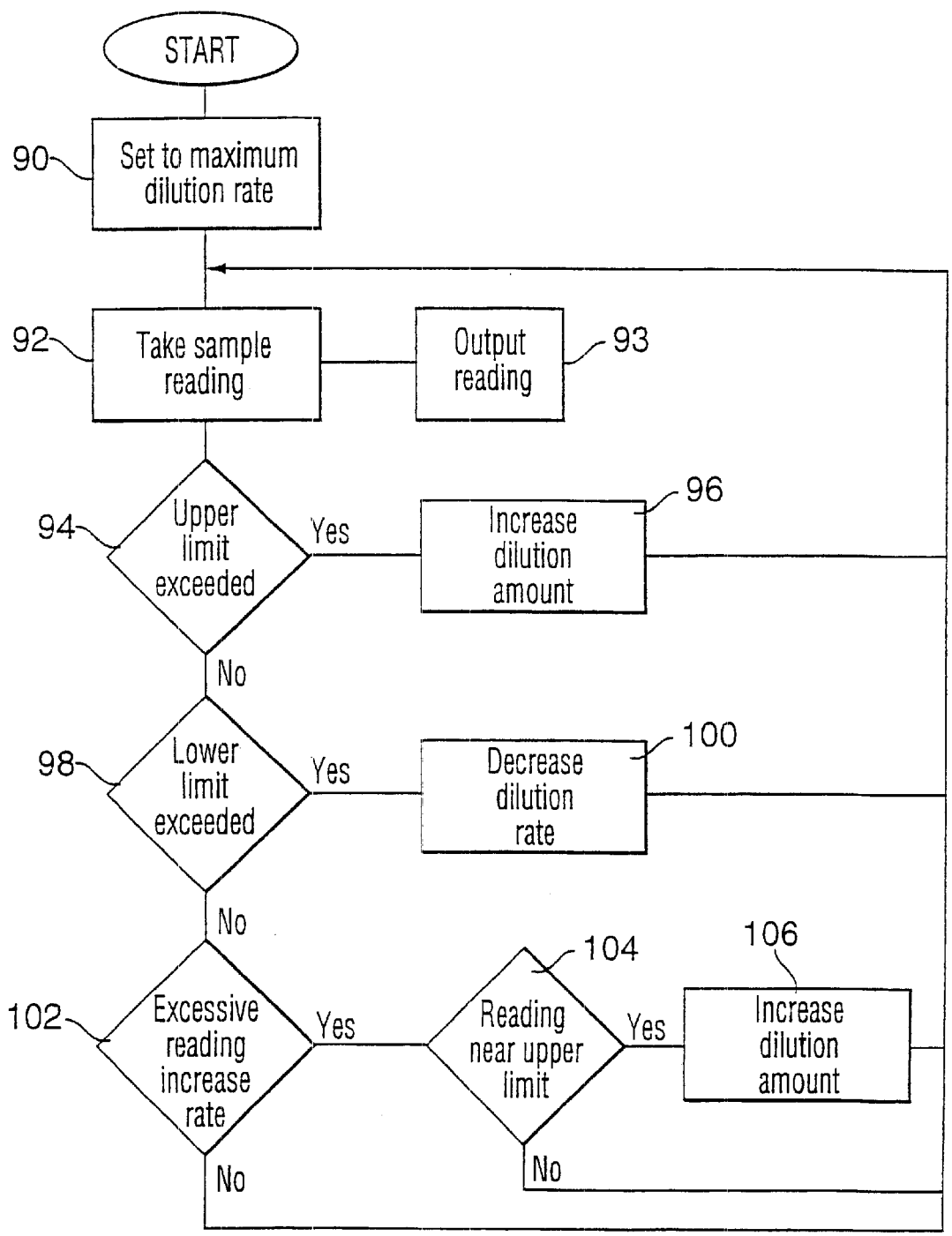
FIG. 3 is a flow chart representation of a control process of the sample dilution system of FIG. 1.

FIG. 3 shows, in flow chart form, aspects of the preferred manner of operation of the sample dilution apparatus controller 44. Setting the maximum dilution setting shown in row 6 of the Dilution Table is performed on sample start as depicted by process box 90. In operation of the controller 44, when the readings in the sensor block detector means 56 fall below a predetermined minimum threshold, for example 1.5%, controller 44 configures the sample dilution apparatus to reduce the mixing ratio, that is, to reduce the amount diluting air mixed with the gas sample. With reference to the Dilution Table, reducing the mixing ratio moves the mixing configuration up one row, for example, from the row 6 configuration to the row 5 configuration. On the other hand, when the mixed sample gas concentration supplied the sensor exceeds the maximum threshold concentration, the next higher mixing ratio is configured by the controller 44.

Dilution Table

| Sample range | Sample MFS % | (ml/min) | Air MFS % | (ml/min) | Exhaust MFS % | (ml/min) |
|---|---|---|---|---|---|---|
| 1 <4% | 100% | (500) | 0% | (0) | % | (0) |
| 2 4–8% | 50% | (250) | 50% | (250) | 50% | (250) |
| 3 8–16% | 25% | (125) | 75% | (375) | 75% | (375) |
| 4 16–32% | 12.5% | (62.5) | 87.5% | (437.5) | 87.5% | (437.5) |
| 5 32–64% | 6.25% | (31.25) | 93.75% | (468.75) | 93.75% | (468.75) |
| 6 64–100 | 3.125% | (15.63) | 96.875% | (484.38) | 96.875% | (484.38) |
| 7 zeroing | 0% | (0) | 100% | (500) | 100% | (500) |

Each row in the table is consecutively numbered and identifies mixing ratios and gas mass flows for the particular mixing configuration. Progressively increasing concentrations of the hydrocarbon combustible gases in the sample are shown row 1 through 6 of the table. Row 7 shows a special zeroing setting that completely closes off sample supply valve 48 thereby preventing any sample from entering to the sensor block detector means 56.

Because CCD sensor elements may suffer damage or burn out when the hydrocarbon percent gas concentrations are greater than 5%, the sample dilution apparatus is configured at start-up to the maximum dilution setting, which is that configuration summarized at row 6 of the Dilution Table. In the configuration of row 6, the gas mixture supplied to the sensor block detector means 56 is diluted to a maximum dilution of the sample and consequently supplies the minimum amount of sample gas to the sensors. In the configuration of row 6, 100% concentrations of hydrocarbon gas in the sample tube 18 will provide no more than 3.125% concentrations of hydrocarbon gas to the sensor block since 3.125% of the sample gas is mixed with 96.875% of the diluting air to provide a maximum mixed gas ratio of 3.125% to the sensor block. Thus in this configuration, a sample gas concentration of 100% hydrocarbon gas will result in a 3.125% concentration of hydrocarbon gas provided to the sensor block detector means 56.

The hydrocarbon gas concentrations in the sample tube 18 can be related to the hydrocarbon gas concentrations provided to the sensor block as follows:

$$S = M * X$$

Where:

X—is the gas concentration of the sample supplied to the sample inlet tube 18

With reference to the Dilution Table, increasing the mixing ratio moves the mixing configuration down one row, for example, from the row 1 configuration to the row 2 configuration.

The lower sample concentration limit in the range indicated in the Sample Range column of Dilution Table is simply a preferred range and does not necessarily cause a reconfiguration to a lower mixing ratio setting, i.e. moving up a row. The lower range limit is arbitrary and it will be understood that the ranges can and do overlap. Switching to a lower mixing ratio, that is moving up a row in the Dilution table, should not occur unless the gas concentration at the sensor block is less than 1.5% at the time of the reconfiguration. If the mixed gas sample concentration at the sensor block detector means 56 is below 2% before a switch to a lower mixing ratio, this avoids providing too rich a mixture to the sensor block detector means 56 at the reconfigured reduced mixing ratio.

On commencement of sample reading, system start-up or after system reset, the mixing ratio is set to the maximum dilution rate by process box 90. A sample reading is obtained from the sensors, as shown by process box 92 and the reading is output. Each time a reading is output, the output reading takes into account the configuration of the sample dilution apparatus to correct the output amount to the reading obtained from the sensor based on the formula $S = M * X$ referred to previously. Process box 93 represents the output of the reading.

The sample reading obtained is then tested against range limits to determine if the sample dilution apparatus requires reconfiguring. At decision box 94, the sample reading is compared to an upper limit. If the upper limit is exceeded, the "Y" exit is taken and the sample dilution apparatus is reconfigured to increase the dilution amount as represented by process box 96 and the next sample is then taken. If the upper limit was not exceeded, then the "N" exit of decision box 94 is taken and the sample reading is then compared to a lower limit at decision box 98. If the sample reading is below the lower limit, the "Y" exit of decision box is taken and the sample dilution apparatus is reconfigured to decrease the dilution rate as depicted by process box 100 and then another sample reading is taken.

To provide a higher degree of control over the hydrocarbon gas concentrations provided to the sensor block, given that a finite period of time will be required to reconfigure the sample dilution apparatus (that is, reconfiguration is not instantaneous), the rate of change of the sample readings can be monitored as well. At decision box 102 the change in the current reading to the previous reading is compared to a change limit. If the reading change shows an increase which exceeds an increase rate limit, the "Y" exit of decision box 102 is taken and the current reading is then evaluated to determined if it is near the upper sensor limit at decision box 104. If the reading is near the upper limit, the "Y" exit is taken and the sample dilution apparatus is reconfigured to increase the dilution amount as depicted by process box 106. This would be equivalent to moving down to the next row in reference to the Dilution Table.

Thus, each sample reading obtained is tested against range limits to determine if the sample dilution apparatus requires reconfiguring. When the sample gas concentration at the sensor block detector means 56 is below the set minimum, controller 44 configures the gas dilution apparatus to mix less diluting air with the sample. The switchover from one mixing ratio to the next is controlled in response to the sensor reading data received from the sensor block detector means 56. The sensor block is thus protected from burnout that would be caused by any percent gas concentrations greater than 5%. By switching over from one range to the other when a predetermined threshold, as for example, a 1.5% threshold is reached, hysteresis problems that might arise when a switchover from one range to another are minimized. Controller 44 may also include a sample readings derivative or differential factor to switch from one range to another when readings appear to be rising or falling quickly so as to ensure that an out of range condition does not occur in sensor block detector means 56.

Figure 4:
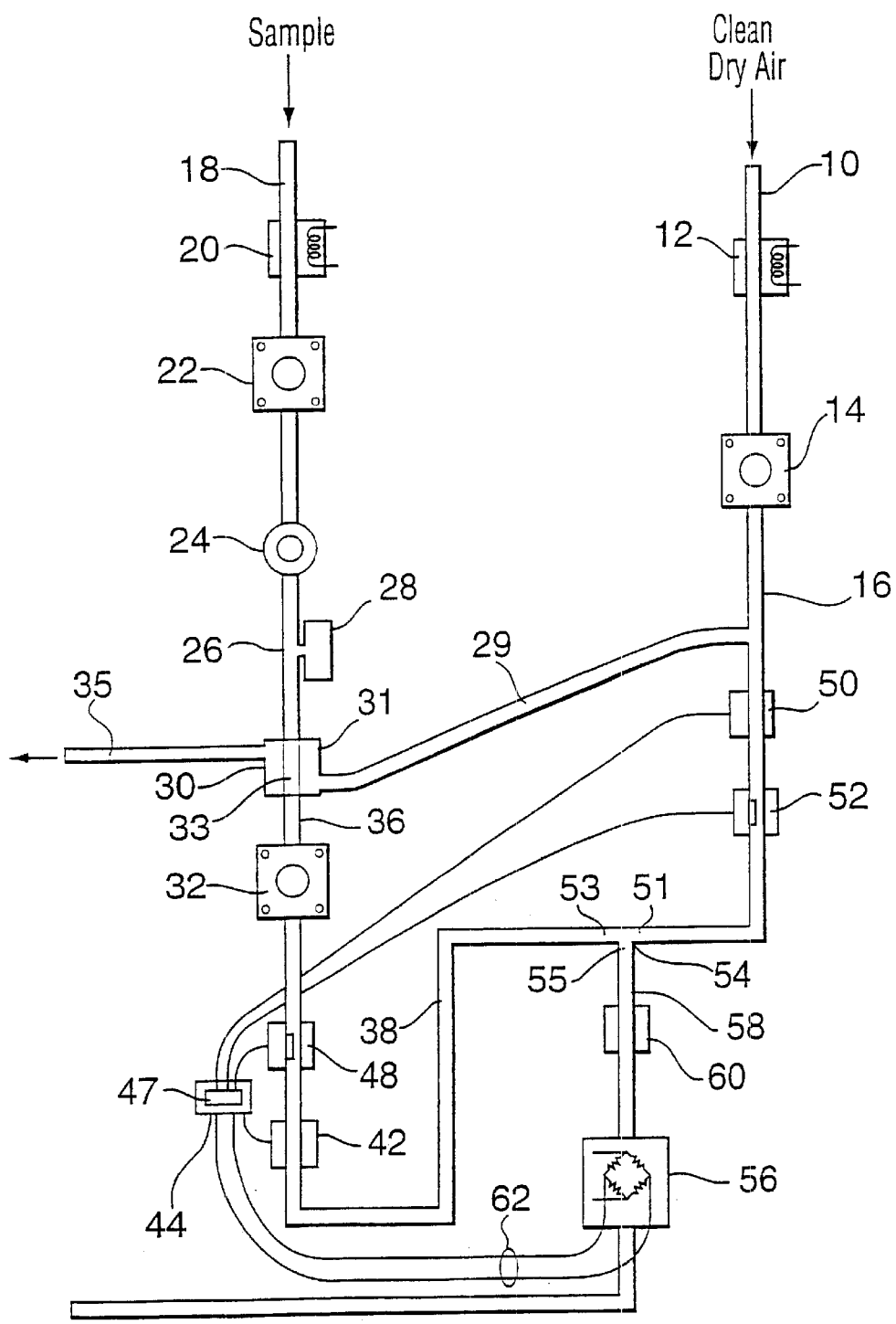
FIG. 4 is a schematic representation of another embodiment of a sample dilution system apparatus incorporating features of the invention without an exhaust gas flow control.

FIG. 4 shows another embodiment of a sample dilution system incorporating features of the invention presented in a schematic diagram form. In this embodiment, no exhaust port is provided in manifold 54. The sample dilution air is supplied under pressure to inlet port 51. The sample gas to be diluted is supplied to sample port 53. The mixed gases exit detector supply port 55 for delivery to the sensor block detector means 56.

In this embodiment, the gas flow rates must change to effect dilution, and for that reason, this arrangement is not the preferred arrangement. For example, the rate of sample gas flow into sample tube 18 must decrease if the rate of mixed gas supply to the sensor block detector means 56 is to be constant for all concentrations of hydrocarbons in the sample gas. Or, in another less preferably method of operation, the rate of mixed gas sample flow into sensor block detector means 56 must increase if the rate of sample gas flow into sample tube 18 is to remain constant for all concentrations of hydrocarbons in the sample gas.

The apparatus is arrange such that a gas flow control means 52 is operated in response to signalling from controller 44 to control the rate of flow of the clean dry diluting air through conduit 16. Manifold 54 forms an inlet port 51 coupled to conduit 16 carrying the diluting air. Inlet port 51 is in communication with common port 53 and detector supply port 55 formed by manifold 54. The supply of diluting air in conduit 16 and sample gas in conduit 38 are combined in manifold 54 and then supplied to the sensor block detector means 56.

It is preferable that the gas flow into detector sample supply line 58 is constant to maintain a constant rate of gas flow into the sensor block detector means 56. A constant rate of gas flow results in a more reliable and repeatable reading from the sensor apparatus. Controller 44 adjusts the mass flow rate, of the diluting air by controlling the dry air gas flow control means valve 52 and of the sample gas by controlling the sample valve gas flow control means 48, to obtain a uniform mass flow rate of the gas mixture into detector sample supply line 58. For example, flow control means valves 48, 52 can be controlled to ensure that a constant flow of gas at the rate of 500 millilitres per minute of gas is presented to detector sample supply line 58. Similar to the embodiment described with reference to FIG. 1, the gas present in detector sample supply line 58 is heated to a uniform temperature by heater 60, for example, to a temperature of 55° C. The heated sample is then presented to sensor block detector means 56, which produces an output representative of the hydrocarbon gases detected in the sample. The sensor block output is supplied to controller 44 on signal line 62 for processing in controller 44. On processing, the controller 44 may output the reading to display 47 for example, or, by supplying the reading in data form on a communications link to a remote computer (not shown) for logging or display.

In the preferred embodiment, controller 44 operates to control the sample valve 48 and air valve 52 such that the sample air ratio is mixed at predetermined amounts. For example, a first ratio when the sample gas is known to be less than 4% can be used for calibration. For calibration, a known 2.5% gas supply is used and fed directly into the gas sample tube 18. In this calibration configuration, controller 44 adjusts the valves of the sample dilution apparatus to provide 100% of the sample volume and 0% of the diluting air volume to the sensor block detector means 56. In this calibration configuration, air supply valve 52 and discharge valve 46 are completely closed and sample valve 48 is completely open. In this configuration of the dilution apparatus, none of the sample is exhausted and no diluting air is mixed with the sample before it enters the sensor block detector means 56.

Below is a Constant Mixed Gas Sample Output Flow Rate Dilution Table (CMGO Dilution Table), which sets out valve configurations that are set in a preferred method of operating the sample dilution apparatus. The sample dilution apparatus valve configuration settings provide an operating range for supply of sample gas to the sensor block detector means 56 to ensure that the maximum hydrocarbon gas concentration supplied to the sensor block detector means 56 does not exceed a 4% concentration. The valve configuration settings provide a lower range, which ensures that the minimum concentration of sample gas supplied to the sensor block detector means 56 does not fall below a predetermined threshold to facilitate obtaining accurate readings from the sensors.

| Constant Mixed Gas Sample Output Flow Rate Dilution Table | | | | |
|---|---|---|---|---|
| Sample | Sample MFS | | Air MFS | |
| range | % | (ml/min) | % | (ml/min) |
| 1  <4% | 100% | (500) | 0% | (0) |
| 2  4–8% | 50% | (250) | 50% | (250) |
| 3  8–16% | 25% | (125) | 75% | (375) |
| 4  16–32% | 12.5% | (62.5) | 87.5% | (437.5) |
| 5  32–64% | 6.25% | (31.25) | 93.75% | (468.75) |
| 6  64–100 | 3.125% | (15.63) | 96.875% | (464.38) |
| 7  Zeroing | 0% | (0) | 100% | (500) |

Each row in the table is consecutively numbered and identifies mixing ratios and gas mass flows for the particular mixing configuration. Progressively increasing concentrations of the hydrocarbon combustible gases in the sample are shown row 1 through 6 of the table. Row 7 shows a special zeroing setting that completely closes off sample supply valve 48 thereby preventing any sample from entering to the sensor block detector means 56.

Because CCD sensor elements may suffer damage or burn out when the hydrocarbon percent gas concentrations are greater than 5%, the sample dilution apparatus is configured at start-up to the maximum dilution setting, which is that configuration summarized at row 6 of the CMGO Dilution Table. In the configuration of row 6, the gas mixture supplied to the sensor block detector means 56 is diluted to a maximum dilution of the sample and consequently supplies the minimum amount of sample gas to the sensors. In the configuration of row 6, 100% concentrations of hydrocarbon gas in the sample tube 18 will provide no more than 3.125% concentrations of hydrocarbon gas to the sensor block as 3.125% of the sample gas is mixed with 96.875% of the diluting air to provide a maximum mixed gas ratio of 3.125% to the sensor block. Thus in this configuration, a sample gas concentration of 100% hydrocarbon gas will result in a 3.125% concentration of hydrocarbon gas provided to the sensor block detector means 56.

In another manner of operation, the controller 44 operates to control the sample valve 48 and air valve 52 such that the sample gas concentration in the mixer port 55 which supplies the mixed sample gas to the sensor block detector means 56 provides an optimal output, for example a 2.5% concentration. In this manner of operation, the mixing ratio of sample gas to diluting gas is continuously variable. The ratio of sample gas to diluting gas is increased until the desired optimal output of the sensor block detector means 56 is obtained. When the desired optimal output is obtained, the mixing ratio of the sample gas to the diluting gas is known, and, consequently, the concentration of the sample gas is determined. Naturally the sample gas concentration may be below the concentration necessary to produce the optimal output of the detector sensor, in which case, the output of the detector sensor will be correspondingly reduced.

Now that the preferred embodiments of the invention have been described numerous changes and modifications may be made thereto without departing from the spirit and scope of the invention as defined in the claims appended hereto.

We claim:

1. A method of measuring a gas mixture comprising:
(i). receiving a sample gas from a source at a predetermined sample gas flow rate;
(ii). supplying a gas mixture to a detector at a predetermined detector supply gas flow rate;
(iii) receiving a detector signalling produced by a detector monitoring the gas mixture supplied by step (ii);
(iv) periodically comparing the received detector signalling to a predetermined range;
(v) mixing a supply of diluting gas with a portion of the sample gas flow to supply the gas mixture at the predetermined detector supply gas flow rate of step (ii) to maintain the received detector signalling within the predetermined range;
whereby the sample gas received in step (i) is received at a predetermined sample gas flow rate and the gas mixture supplied to the detector is supplied at a predetermined detector supply gas flow rate.

2. The method of claim 1 further wherein the predetermined range has an upper threshold.

3. The method of claim 2 wherein the upper threshold is 4 percent.

4. The method of claim 2 wherein the gas mixture supplied to the detector is supplied at a gas flow rate obtained by mixing a supply of diluting gas with a portion of the sample gas flow to supply the gas mixture at a predetermined amount selected from one of:

(1) 100 percent sample gas mixed with 0 percent diluting gas;

(2) 50 percent sample gas mixed with 50 percent diluting gas;

(3) 25 percent sample gas mixed with 75 percent diluting gas;

(4) 12.5 percent sample gas mixed with 87.5 percent diluting gas;

(5) 6.25 percent sample gas mixed with 93.75 percent diluting gas;

(6) 3.125 percent sample gas mixed with 96.875 percent diluting gas; and (7) 0 percent sample gas mixed with 100 percent diluting gas.

5. The method of claim 2 further including the steps of:
(i) periodically comparing the received detector signalling to the upper threshold and when the received detector signalling exceeds the upper threshold:
(i.1) reducing the portion of the sample gas flow mixed with the supply of diluting gas when the periodic comparison of the received detector signalling is above a predetermined, and
(i.2) increasing the supply of diluting gas;
whereby continuous receipt of sample gas is obtained at a predetermined sample gas flow rate.

6. The method of claim 1 further wherein the predetermined range has a lower threshold.

7. The method of claim 6 wherein the lower threshold is 1.5 percent.

8. The method of claim 6 further including the steps of:
(i) periodically comparing the received detector signalling to the lower threshold and when the received detector signalling is below the lower threshold:
(i.1) increasing the portion of the sample gas flow mixed with the supply of diluting gas when the periodic comparison of the received detector signalling is above a predetermined, and
(i.2) decreasing the supply of diluting gas,
whereby continuous receipt of sample gas is obtained at a predetermined sample gas flow rate.

9. The method of claim 6 wherein the gas mixture supplied to the detector is supplied at a gas flow rate obtained by mixing a supply of diluting gas with a portion of the sample gas flow to supply the gas mixture at a predetermined amount selected from one of:
   (1) 100 percent sample gas mixed with 0 percent diluting gas;
   (2) 50 percent sample gas mixed with 50 percent diluting gas;
   (3) 25 percent sample gas mixed with 75 percent diluting gas;
   (4) 12.5 percent sample gas mixed with 87.5 percent diluting gas;
   (5) 6.25 percent sample gas mixed with 93.75 percent diluting gas;
   (6) 3.125 percent sample gas mixed with 96.875 percent diluting gas; and
   (7) 0 percent sample gas mixed with 100 percent diluting gas.

* * * * *